United States Patent
Wu et al.

(10) Patent No.: US 10,590,451 B2
(45) Date of Patent: Mar. 17, 2020

(54) METHODS OF CONSTRUCTING A CIRCULAR TEMPLATE AND DETECTING DNA MOLECULES

(71) Applicant: Personal Genomics, Inc., Grand Cayman (KY)

(72) Inventors: Mengchu Wu, Hsinchu (TW); Meng-Tsung Tien, Hsinchu County (TW)

(73) Assignee: Personal Genomics, Inc., Grand Cayman (KY)

( * ) Notice: Subject to any disclaimer, the term of this patent is extended or adjusted under 35 U.S.C. 154(b) by 238 days.

(21) Appl. No.: 15/638,392

(22) Filed: Jun. 30, 2017

(65) Prior Publication Data

US 2018/0002731 A1 Jan. 4, 2018

Related U.S. Application Data

(60) Provisional application No. 62/357,382, filed on Jul. 1, 2016.

(51) Int. Cl.

| | |
|---|---|
| *C12Q 1/68* | (2018.01) |
| *C12P 19/34* | (2006.01) |
| *C12Q 1/6806* | (2018.01) |
| *C12Q 1/6853* | (2018.01) |
| *C12Q 1/6855* | (2018.01) |
| *C12Q 1/686* | (2018.01) |
| *C12Q 1/6869* | (2018.01) |

(52) U.S. Cl.
CPC ............ *C12P 19/34* (2013.01); *C12Q 1/6806* (2013.01); *C12Q 1/686* (2013.01); *C12Q 1/6853* (2013.01); *C12Q 1/6855* (2013.01); *C12Q 1/6869* (2013.01); *C12Q 1/68* (2013.01); *C12Q 2521/501* (2013.01); *C12Q 2525/307* (2013.01)

(58) Field of Classification Search
CPC ............ C12Q 1/6855; C12Q 2521/501; C12Q 2525/307
See application file for complete search history.

(56) References Cited

U.S. PATENT DOCUMENTS

| | | | |
|---|---|---|---|
| 5,714,320 A | 2/1998 | Kool | |
| 7,303,901 B2 | 12/2007 | Hjorleifsdottir et al. | |
| 9,217,167 B2 | 12/2015 | Heller et al. | |
| 2008/0171331 A1* | 7/2008 | Drmanac | C12N 15/10 435/5 |
| 2013/0309678 A1 | 11/2013 | Travers et al. | |

FOREIGN PATENT DOCUMENTS

| | | |
|---|---|---|
| CN | 102317475 | 1/2012 |
| CN | 104946737 | 9/2015 |
| CN | 105392901 | 3/2016 |
| WO | 2008058282 | 5/2008 |
| WO | 2014093186 | 6/2014 |
| WO | 2015089333 | 6/2015 |

OTHER PUBLICATIONS

"Office Action of Taiwan Counterpart Application," dated Apr. 19, 2018, p. 1-p. 12.

* cited by examiner

*Primary Examiner* — David C Thomas
(74) *Attorney, Agent, or Firm* — JCIPRNET

(57) ABSTRACT

A method of constructing a circular template includes preparing a partially double stranded linear DNA molecule, and incubating the partially double stranded linear DNA molecule with a ligase capable of intra-molecular ligation of single stranded DNA molecules to generate a partially double stranded circular DNA molecule. A method of detecting DNA molecules includes the following steps. Target DNA molecules are isolated with probes to form partially double stranded linear DNA molecules. The partially double stranded linear DNA molecules are incubated with ligases capable of intra-molecular ligation of single stranded DNA molecules to generate partially double stranded circular DNA molecules. A circular sequencing of the partially double stranded circular DNA molecules is conducted by using the probes as primers.

11 Claims, 11 Drawing Sheets

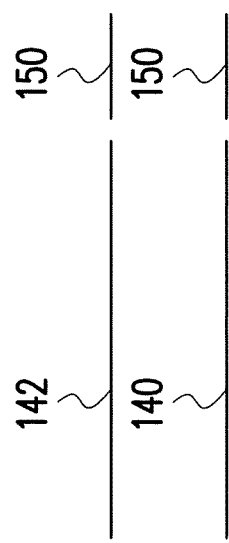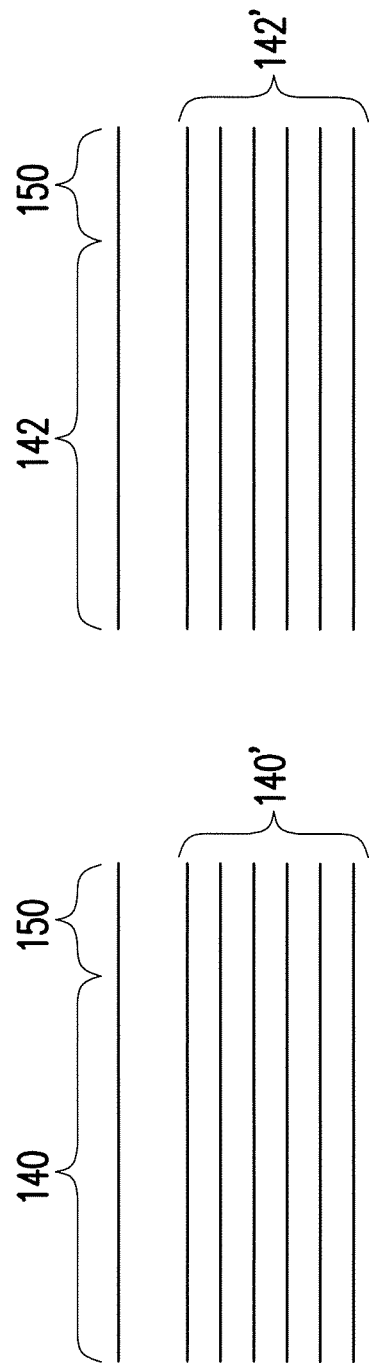

METHODS OF CONSTRUCTING A CIRCULAR TEMPLATE AND DETECTING DNA MOLECULES

CROSS REFERENCE TO RELATED APPLICATION

This application claims the priority benefit of U.S. provisional application Ser. No. 62/357,382, filed on Jul. 1, 2016. The entirety of the above-mentioned patent application is hereby incorporated by reference herein and made a part of specification.

BACKGROUND OF THE INVENTION

Field of the Invention

The invention relates to a method of constructing DNA and a method of detecting DNA, in particular, to a method of constructing a circular template and a method of detecting DNA molecules, preferably fragmented DNA molecules, such as cell free DNA molecules.

Description of Related Art

With the development of precision medicine and the importance of individualized medicine, gene sequencing techniques are widely used. By comparing and analyzing the genetic information of individual and databases to detect whether the individual's genetic sequence has a harmful genetic mutation such as rare tumor derived mutations. Therefore, the disease can be prevented or treated early.

However, current library construction and sequencing methods are labor intensive and high cost and may produce bias such as amplification bias. Therefore, the development of new gene sequencing methods to achieve the purpose of high accuracy, rapid reaction, or low cost is the current urgent problem to be solved.

SUMMARY OF THE INVENTION

The invention provides a method of constructing a circular template to generate a partially double stranded circular DNA molecule for circular amplification or circular sequencing.

The invention provides a method of detecting DNA molecules, preferably fragmented DNA molecules, such as cell free DNA molecules. The method provided herein has advantages of high accuracy, rapid reaction, low cost, and less bias. The methods provided herein can detect both single stranded and double stranded DNA in one sample.

The invention provides a method of constructing a circular template and the method includes the following steps. A partially double stranded linear DNA molecule is prepared, and the partially double stranded linear DNA molecule includes single stranded protruding portions at both ends on the same strand. The partially double stranded linear DNA molecule is incubated with a ligase capable of intra-molecular ligation of single stranded DNA molecules to generate a partially double stranded circular DNA molecule.

In an embodiment of the invention, the method of preparing the partially double stranded linear DNA molecule includes providing a single stranded linear DNA molecule and hybridizing a probe to the single stranded linear DNA molecule.

In an embodiment of the invention, the single stranded linear DNA molecule includes 40 nucleotides to 500 nucleotides in length.

In an embodiment of the invention, the probe includes 20 nucleotides to 120 nucleotides in length.

In an embodiment of the invention, the probe includes a biotinylated probe.

In an embodiment of the invention, after hybridizing the probe to the single stranded linear DNA molecule, the partially double stranded linear DNA molecule is extracted by a streptavidin bead.

In an embodiment of the invention, the method of preparing the partially double stranded linear DNA molecule includes the following steps. A double stranded linear DNA molecule is provided. A first adaptor and a second adaptor are provided, wherein the first adaptor and the second adaptor have a double stranded portion and a single stranded protruding portion at one end. The first adaptor is ligated to one end of the double stranded linear DNA molecule and the second adaptor is ligated to the other end to form the partially double stranded linear DNA molecule. The single stranded protruding portion of the first adaptor and the single stranded protruding portion of the second adaptor are then on the same strand of the partially double stranded linear DNA molecule.

In an embodiment of the invention, the first and the second adaptors include at least 20 nucleotides of single protruding stranded portion at one end.

In an embodiment of the invention, the first adaptor or the second adaptor is conjugated with a biotinylated label, and the partially double stranded linear DNA molecule is then extracted by a streptavidin bead.

In an embodiment of the invention, a step of removing the single stranded DNA molecule which are not hybridized with the probes is further included.

In an embodiment of the invention, the partially double stranded linear DNA molecule includes at least 10 nucleotides of single stranded protruding portions at the both ends.

In an embodiment of the invention, the ligase is a single stranded DNA ligase.

The invention provides another method of detecting DNA molecules and the method includes the following steps. Target DNA molecules are isolated with probes to form partially double stranded linear DNA molecules. The partially double stranded linear DNA molecules are incubated with ligases capable of intra-molecular ligation of single stranded DNA molecules to generate partially double stranded circular DNA molecules. Circular sequencing of the partially double stranded circular DNA molecules is conducted by using the probes as primers.

In an embodiment of the invention, the probes are biotinylated probes, and the method of isolating the target DNA molecules with the probes includes the following steps. A plurality of oligonucleotides is provided. The oligonucleotides are ligated to the target DNA molecules, wherein the target DNA molecules are single stranded linear DNA molecules. The target DNA molecules are amplified. The biotinylated probes are hybridized to the target DNA molecules.

In an embodiment of the invention, the target DNA molecules are extracted from clinical specimens which include liquid biopsies or stool.

In an embodiment of the invention, the liquid biopsies include plasma, saliva, or urine.

Based on the above, the invention provides a method of constructing circular templates for sequencing, which includes providing partially double stranded linear DNA molecules and generating partially double stranded circular DNA molecules therefrom by using single stranded DNA ligases. The invention also provides a method of detecting DNA molecules, which includes hybridizing a probe to a region of interest of each DNA molecule, generating partially double stranded circular DNA molecules therefrom by using ligases, in particularly single stranded DNA ligases, and conducting circular sequencing. The method of constructing a circular template and the method of detecting DNA molecules provided in present invention have the advantage of high accuracy, rapid reaction, or low cost.

In order to make the aforementioned features and advantages of the invention more comprehensible, embodiments are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIGS. 5A-5E illustrate the method of detecting DNA molecules according to an embodiment of the invention.

DESCRIPTION OF THE EMBODIMENTS

The invention provides a method for constructing a circular template and a method for detecting DNA molecules. To facilitate understanding of the description of the invention, the following definitions are provided.

"Circular sequencing" is a sequencing reaction utilizing circular templates. For example, circular sequencing includes DNA nanoball sequencing adopted by BGI, or SMRT sequencing adopted by Pacific Biosciences.

"Ligation" is an action of forming a phosphodiester bond or linkage between the termini of two nucleic acids such as oligonucleotides or polynucleotides. The ligation may be carried out by enzyme such as DNA ligases.

"Hybridization (or hybridizing)" is a reaction that oligonucleotides or polynucleotides such as DNA or RNA anneal to the complementary oligonucleotides or polynucleotides.

"Primer" is a short polynucleotide with about 10-100 nucleotides in length. Primer binds to a target polynucleotide or "template" by hybridizing with the target. The primer preferably provides a starting point for DNA synthesis of a polynucleotide complementary to the target, which can take place in the presence of a DNA polymerase. The DNA polymerase typically adds and extend new nucleotides to the 3' end of the primer. The 3' end of the primer also serves as a substrate for DNA ligases.

"DNA sequencing" is a reaction of determining the nucleotides of DNA. For example, the reaction typically includes a set of cycles of annealing, extension, and detection; the sequence specific primers are used for annealing; the DNA polymerase and the fluorescent signal labelled nucleotides are used for extension; and the fluorescent signal is used as indicator for detection.

"Biotin-Streptavidin interaction" is used in many nucleic acid and protein purification method. Biotin is small and shows rare interference with the biotin labelled molecule. Streptavidin shows high specificity and affinity to bind biotin, so that streptavidin conjugated beads are typically used to isolate and purified the biotin labelled molecule from the mixture.

FIGS. 1A-1D illustrate a method of constructing a circular template according to an embodiment of the invention.

Figure 1A:
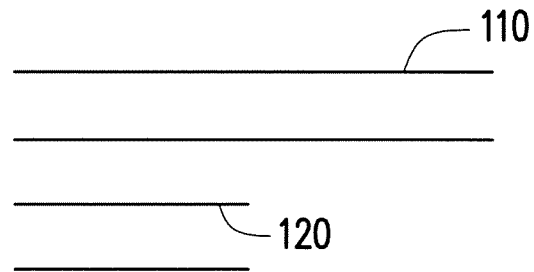
FIGS. 1A-1D illustrate the method of constructing a circular template according to an embodiment of the invention.

Referring to FIG. 1A, a single stranded linear DNA 110 and a probe 120 are provided. The single stranded linear DNA molecule 110 includes 40 nucleotides to 500 nucleotides in length, for example. In some embodiment, the single stranded linear DNA molecule 110 includes 40 nucleotides to 200 nucleotides in length, for example. The probe 120 includes 20 nucleotides to 120 nucleotides in length, for example. In some embodiments, the probe 120 includes 20, 40, 60, 80, 100, or 120 nucleotides. In some embodiments, the single stranded linear DNA molecule is 100 nucleotides in length, and the probe is 20, 40, 60, 80, 100, or 120 nucleotides in length.

Figure 1B:
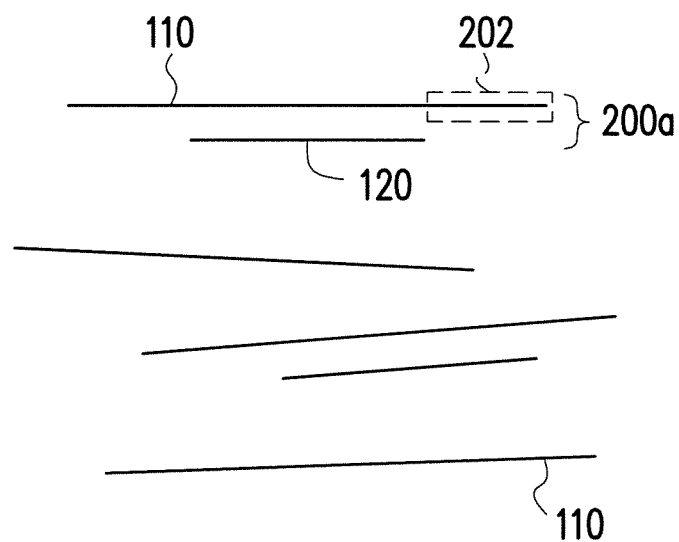

Referring to FIG. 1B, a probe 120 is hybridized to a single stranded linear DNA molecule 110 to form a partially double stranded linear DNA molecule 200a. In some embodiments, the partially double stranded linear DNA molecule 200a includes single stranded protruding portions 202 at both ends on the same strand. In other words, the double stranded linear DNA has protruded single stranded protruding portions 202 at both ends of one strand. In some embodiments, each of the single stranded protruding portion 202 includes at least 5 nucleotides or at least 10 nucleotides, for example, preferably at least 15 or 20 nucleotides. A length of the partially double stranded linear DNA molecule 200a is equal to or less than 500 nucleotides. In some embodiments, a length of the partially double stranded linear DNA molecule 200a is equal to or less than 200 nucleotides. In some embodiments, after hybridization reaction, there are some remained single stranded linear DNA molecules 110 which are not hybridized with the probes 120. In other word, the partially double stranded linear DNA molecules 200a and the remained single stranded linear DNA molecules 110 may be co-existed after hybridization reaction. In alternative embodiments, if required, the remained single stranded linear DNA molecules 110 may be removed after hybridization.

Figure 1C:
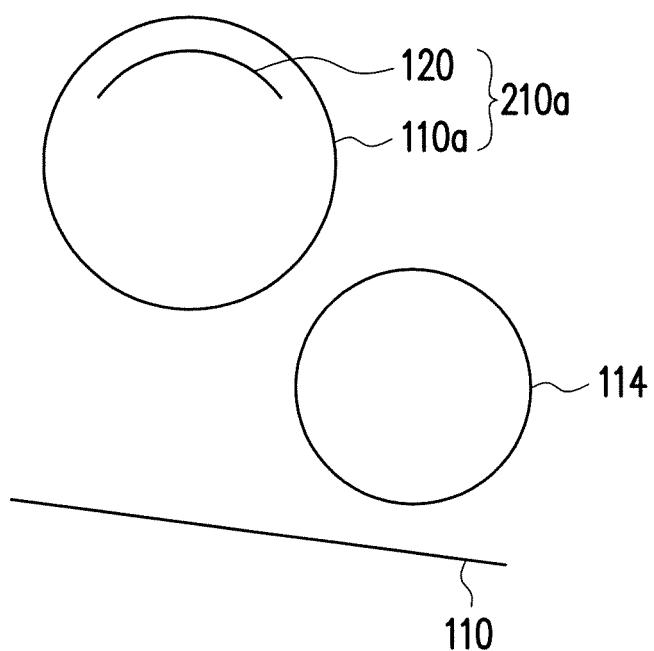

Referring to FIG. 1C, the partially double stranded linear DNA molecules 200a are incubated with ligases. In some embodiments, the remained single stranded linear DNA molecules 110 are also incubated with the ligases. The ligases are capable of performing an intra-molecular ligation to ligate the single stranded DNA molecules, that is, the single stranded DNA molecules are substrates of the ligases. In some embodiments, the ligases are single stranded DNA ligases such as CircLigase (for example, CircLigase I and II). The ligases are used to ligate the single stranded protruding portions of the partially double stranded linear DNA molecules 200a to generate partially double stranded circular DNA molecules 210a. In some embodiments, the partially double stranded circular DNA molecule 210a includes a single strand circular DNA molecule 110a formed from the single stranded linear DNA molecule 110 and a single strand linear DNA molecule which is the probe 120. In some embodiments, the partially double stranded circular DNA molecules 210a are equal to or less than 500 nucleotides. In some embodiments, the partially double stranded circular DNA molecules 210a are equal to or less than 200 nucleotides. It is noted that the ligases also ligate the remained single stranded linear DNA molecules 110 to generate single stranded circular DNA molecules 114. However, as shown in FIG. 1C, there may be still some single stranded linear DNAs molecules 110 unligated and remained, but the invention is not limited thereto.

Figure 1D:
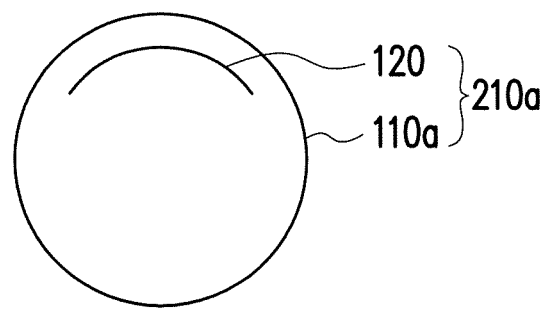

Referring to FIG. 1D, the partially double stranded circular DNA molecule 210a is sequenced. In some embodiments, the probe 120 is directly used as a primer for sequencing. In some embodiments, if required, exonuclease is used to remove the unligated single stranded linear DNA molecules 110.

In some embodiments, the sequencing of the single stranded linear DNA molecules 110 is performed by forming the partially double stranded circular DNA molecules 210a including the single stranded linear DNA molecules 110 and the probes 120 and sequencing the partially double stranded circular DNA molecules 210a. Since the probes 120 can act as primers directly, the additional priming step is not required. Accordingly, the invention provides a method of constructing and sequencing a circular template with reduced reaction time and cost.

FIGS. 2A-2E illustrate a method of constructing a circular template according to another embodiment of the invention. The method of FIGS. 2A-2E is similar to the method of FIGS. 1A-1D, and therefore the same components are labelled by the same reference numbers. The main difference between the method of FIGS. 2A-2E and the method of FIGS. 1A-1D is that the method of FIGS. 2A-2E uses biotinylated probes and streptavidin beads, and the step of using the exonuclease is optional.

Figure 2A:
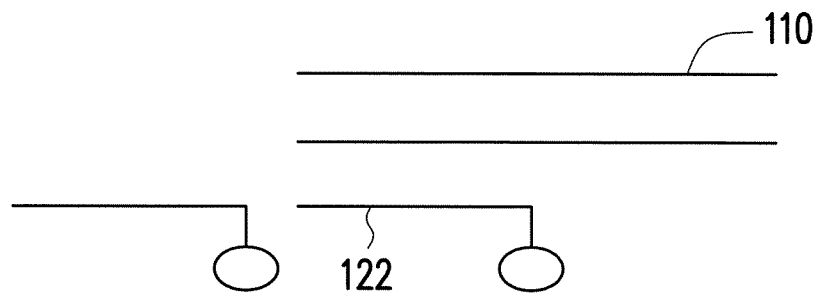
FIGS. 2A-2E illustrate the method of constructing a circular template according to another embodiment of the invention.

Referring to FIG. 2A, single stranded linear DNA molecules 110 and biotinylated probes 122 are provided. The biotinylated probes 122 are probes labelled with a biotin.

Figure 2B:
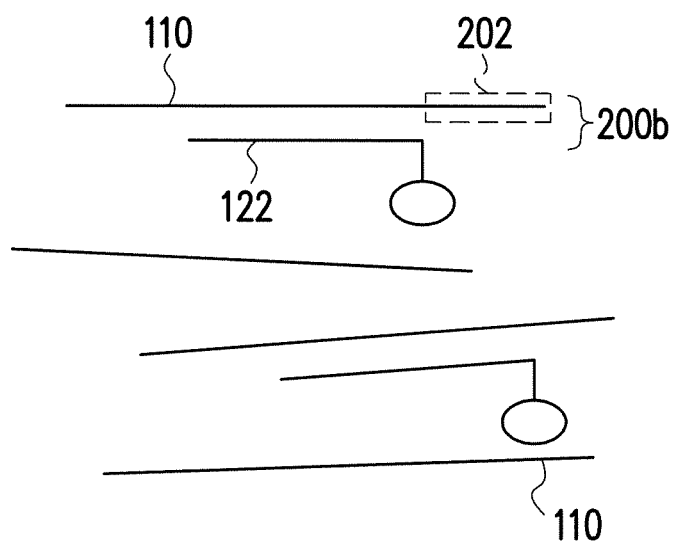

Referring to FIG. 2B, a biotinylated probe 122 is hybridized to a single stranded linear DNA molecule 110 to form a partially double stranded linear DNA molecule 200b. The partially double stranded linear DNA molecule 200b includes single stranded protruding portions 202 at both ends. In some embodiments, after hybridization reaction, there are some remained single stranded linear DNA molecules 110 which are not hybridized with the biotinylated probes 122. In other word, the partially double stranded linear DNA molecules 200b and the remained single stranded linear DNA molecules 110 may be co-existed after hybridization reaction. In alternative embodiments, if required, the remained single stranded linear DNA molecules 110 may be removed after hybridization.

Figure 2C:
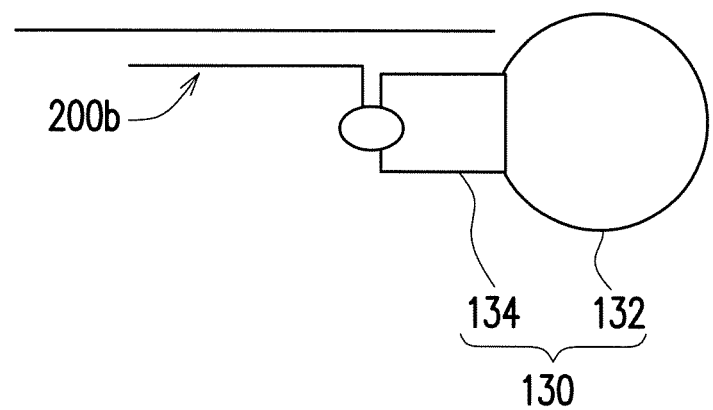

Referring to FIG. 2C, streptavidin beads 130 are used to extract the partially double stranded linear DNA molecules 200b including the biotinylated probe 122. In some embodiments, the streptavidin beads 130 are the bead 132 conjugated with the streptavidin 134, and the streptavidin bead 130 is a streptavidin magnetic bead, for example. During the extracting, the partially double stranded linear DNA molecules 200b are interacted with the streptavidin beads 130 through the biotinylated probes 122, and the remained single stranded linear DNA molecules 110 which do not interact with the streptavidin beads 130 are removed. The removal method of the remained single stranded linear DNA molecules 110 includes buffer washing.

Figure 2D:
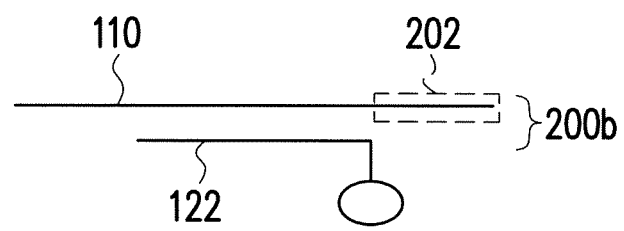
Figure 2D:
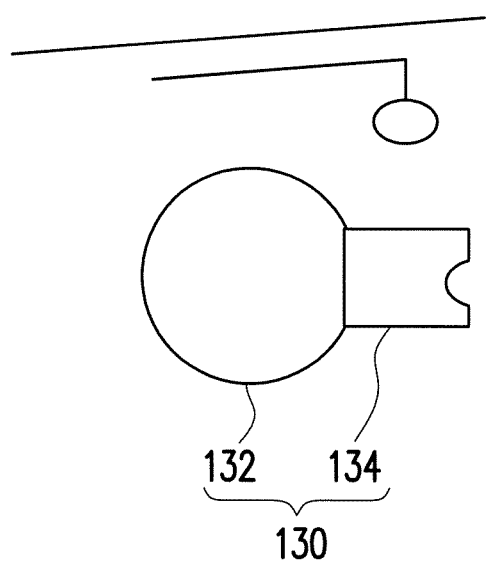

Referring to FIG. 2D, after extracting, the partially double stranded linear DNA molecules 200b are dissociated from the streptavidin beads 130. In some embodiments, a dissociating method is a heating process, for example.

Figure 2E:
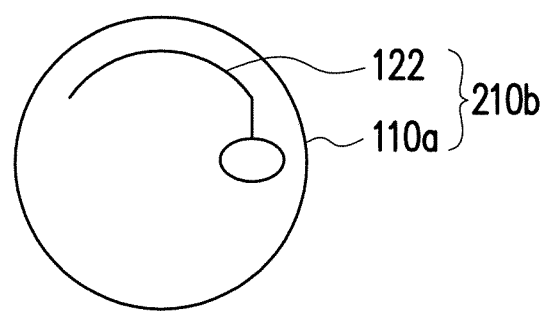

Referring to FIG. 2E, ligases are used to ligate the single stranded protruding portions 202 of the partially double stranded linear DNA molecules 200b to generate partially double stranded circular DNA molecules 210b. In some embodiments, the partially double stranded circular DNA molecule 210b includes a single strand circular DNA molecule 110a formed from the single stranded linear DNA molecule 110 and a single strand linear DNA molecule which is the biotinylated probe 122. Since the remained single stranded linear DNA molecules 110 are removed in the previous step, it is optional to use exonuclease to remove the single stranded DNA molecules 110.

Then, the partially double stranded circular DNA molecules 210b are sequenced. In some embodiments, the biotinylated probes 122 are directly used as primers for sequencing.

In some embodiments, the sequencing of the single stranded linear DNA molecule 110 is performed by forming the partially double stranded circular DNA molecule 210b including the single stranded linear DNA molecule 110 and the biotinylated probe 122 and sequencing the partially double stranded circular DNA molecule 210b. Since the biotinylated probes 122 can act as primers directly, the additional priming step is not required. Accordingly, the method of constructing a circular template has reduced reaction time and cost. It is note that although the biotin is used as a tagging target molecular in some embodiments, the invention is not limited thereto.

Figure 3A:
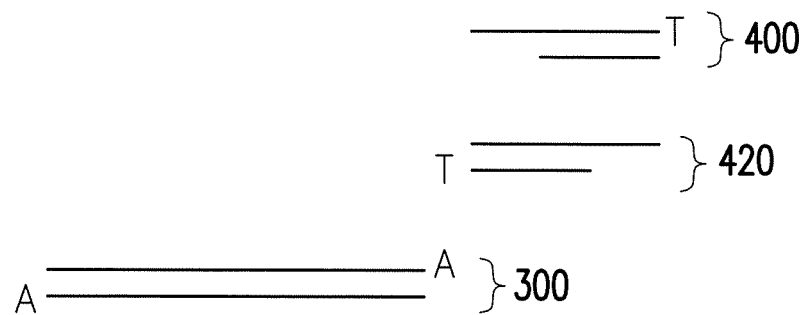
FIGS. 3A-3C illustrate the method of constructing a circular template according to another embodiment of the invention.
Figure 3B:
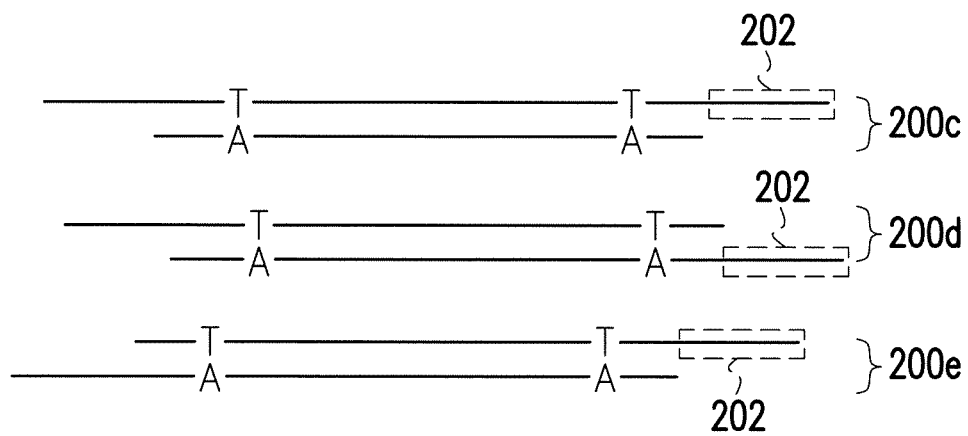
Figure 3C:
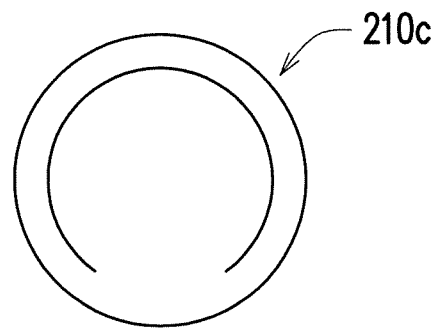

FIGS. 3A-3C illustrate a method of constructing a circular template according to another embodiment of the invention.

Referring to FIG. 3A, a double stranded linear DNA 300 and adaptors (400, 420) are provided. In some embodiments, A-tail is respectively added to the both ends of a double stranded linear DNA to generate the double stranded linear DNA 300 with A-tail. That is, the A-tail is formed by adding at least one adenine nucleotide to the both 3' ends of the double stranded linear DNA respectively. The adaptors (400, 420) have a double stranded portion and a single stranded protruding portion at one end. In some embodiments, each of the adaptors (400, 420) is a double stranded DNA with T-tail at one end and a single stranded protruding portion at the other end, for example. In some embodiments, T-tail may be formed by adding at least one thymine nucleotide to one of the two 3' ends of the adaptors (400, 420). The single stranded protruding portion of the adaptors (400, 420) may include at least 10 nucleotides, preferably at least 20 nucleotides.

In some embodiments, the adaptor 400 has 5' single stranded protruding portion and 3' T-tail in the same strand of the double stranded DNA, for example. The adaptor 420 has 3' single stranded protruding portion in the one strand of the double stranded DNA and 3' T-tail in the other strand of the double stranded DNA, for example. However, the invention is not limited thereto.

Referring to FIG. 3B, the adaptors (400, 420) are ligated to both ends of the double stranded linear DNA 300 to form the partially double stranded linear DNA molecules (200c, 200d, 200e). In some embodiments, one adaptor (400, 420) is ligated to one end of the double stranded linear DNA 300, and the other adaptor (400, 420) is ligated to the other end of the double stranded linear DNA 300. In some embodiments, the partially double stranded linear DNA molecules (200c, 200d, 200e) include single stranded protruding portions 202 at both ends. In some embodiments, each of the single stranded protruding portions 202 includes at least 5 nucleotides or at least 10 nucleotides, preferably at least 20 nucleotides. In some embodiments, a length of the partially double stranded linear DNA molecules (200c, 200d, 200e) is equal to or less than 500 nucleotides. In some embodiments, a length of the partially double stranded linear DNA molecules (200c, 200d, 200e) is equal to or less than 200 nucleotides.

In some embodiments, different partially double stranded linear DNA molecules (200c, 200d, 200e) are formed. In detail, the partially double stranded linear DNA molecules 200c are formed by ligating the adaptor 400 to one end of the double stranded linear DNA 300 and ligating the adaptor 420 to the other end of the double stranded linear DNA 300. The partially double stranded linear DNA molecules 200d are formed by ligating the first adaptors 400 to the both ends of the double stranded linear DNA 300. The partially double stranded linear DNA molecules 200e are form by ligating the second adaptor 420 to the both ends of the double stranded linear DNA 300.

Among the partially double stranded linear DNA molecules (200c, 200d, 200e), the partially double stranded linear DNA molecules 200c include single stranded protruding portions 202 at both ends on the same strand, that is, the partially double stranded linear DNA molecules 200c have one strand longer than another strand at both ends. Thus, the partially double stranded linear DNA molecules 200c can be the substrate of single stranded DNA ligases such as CircLigase, which are capable of performing an intra-molecular ligation to ligate the single stranded DNA.

Referring to FIG. 3C, the ligases are used to ligate the single stranded protruding portions 202 of the partially double stranded linear DNA molecules 200c to generate partially double stranded circular DNA molecules 210c. In some embodiments, the partially double stranded circular DNA molecules 210c include a single strand circular DNA and a single strand linear DNA which are formed from the double stranded linear DNA 300 and adaptors (400, 420). In some embodiments, a length of the partially double stranded circular DNA molecules 210c is equal to or less than 500 nucleotides. In some embodiments, a length of the partially double stranded circular DNA molecules 210c is equal to or less than 200 nucleotides.

Then, the partially double stranded circular DNA molecules 210c are sequenced. In some embodiments, the shorter strand of the partially double stranded circular DNA molecules 210c is directly used as a primer for sequencing.

In some embodiments, the sequencing of the double stranded linear DNA 300 is performed by forming the partially double stranded circular DNA molecule 210c including the double stranded linear DNA 300 and adaptors (400, 420) and sequencing the partially double stranded circular DNA molecule 210c. Since the shorter strand DNA of the partially double stranded circular DNA molecule 210c can act as a primer directly, the additional priming step is not required. Accordingly, the reaction time and cost are reduced.

FIGS. 4A-4E illustrate a method of constructing a circular template according to another embodiment of the invention. The method of FIGS. 4A-4E is similar to the process of FIGS. 3A-3C, and therefore the same components are labelled by the same reference numbers. The main difference between the process of FIGS. 4A-4E and the process of FIGS. 3A-3C is that the process of FIGS. 4A-4E uses a biotinylated adaptor and streptavidin beads.

Figure 4A:
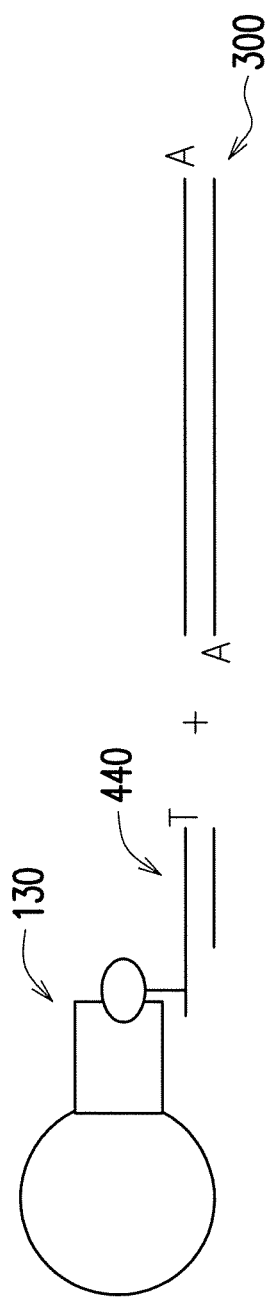
FIGS. 4A-4E illustrate the method of constructing a circular template according to another embodiment of the invention.

Referring to FIG. 4A, a double stranded linear DNA 300 and an adaptor 440 are provided. In some embodiments, the adaptor 440 is a partially double stranded DNA which has a single stranded protruding portion. In detail, the adaptor 440 has a T-tail at 3' end and a biotinylated label at 5' end of the single stranded protruding portion, and the biotinylated label is linked to the streptavidin beads 130, for example.

Figure 4B:
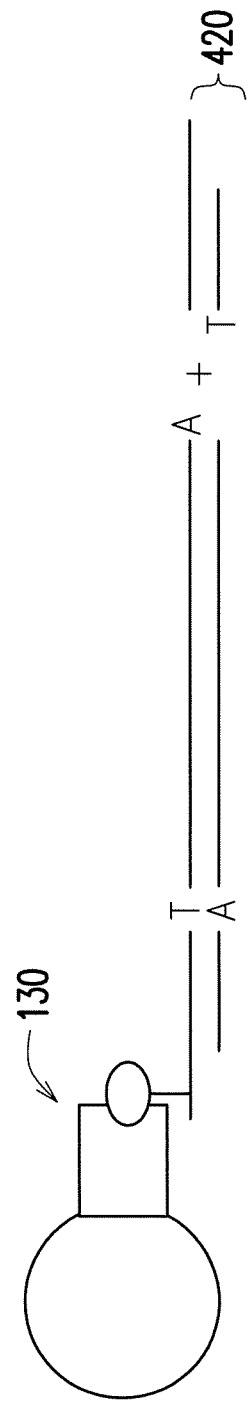

Referring to FIG. 4B, the adaptor 440 is ligated to one end of the double stranded linear DNA 300. In some embodiments, the T-tail of the adaptor 440 is paired with the A-tail of the double stranded linear DNA 300, so that the adaptor 440 and the double stranded linear DNA 300 are ligated.

Then, another adaptor 420 is provided. In some embodiments, the adaptor 420 is the same as that in FIG. 3A, and thus the description thereof is omitted.

Figure 4C:
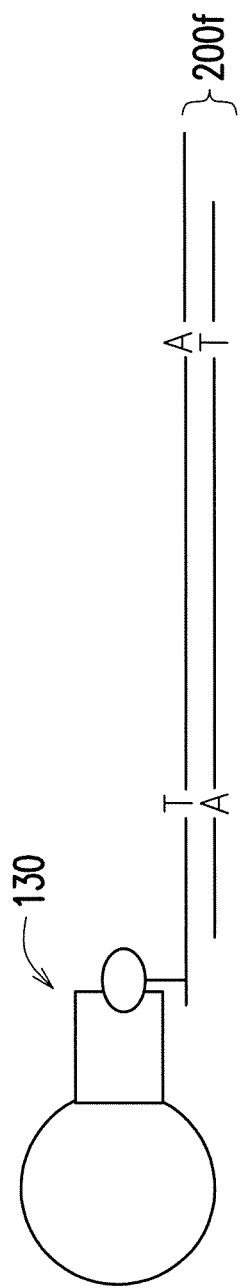

Referring to FIG. 4C, the adaptor 420 is ligated to the other end of the double stranded linear DNA 300 which is ligated with the adaptor 440, so as to form a partially double stranded linear DNA molecule 200f. In some embodiments, the T-tail of the adaptor 420 is paired with the exposed A-tail of the double stranded linear DNA 300, and thus the adaptor 420 and the double stranded linear DNA 300 are ligated. In other words, one end of the double stranded linear DNA 300 is ligated with the adaptor 420, and the other end of the double stranded linear DNA 300 is ligated with the adaptor 440 which is linked to the streptavidin beads 130. Accordingly, the partially double stranded linear DNA molecules 200f associated with the streptavidin beads 130 are generated and is extracted by using buffer to remove the unligated adaptor 420 and the unligated adaptor 440.

In some embodiments (not shown), the adaptor 400 without a biotinylated label is used to replace the adaptor 440 with the biotinylated label to ligate to one end of the double stranded linear DNA 300. The biotinylated label is linked to the streptavidin beads 130, for example. The adaptor 420 with a biotinylated label at 3' end of the single stranded protruding portion is used to replace the adaptor 420 without a biotinylated label to ligate to the other end of the double stranded linear DNA 300.

Figure 4D:
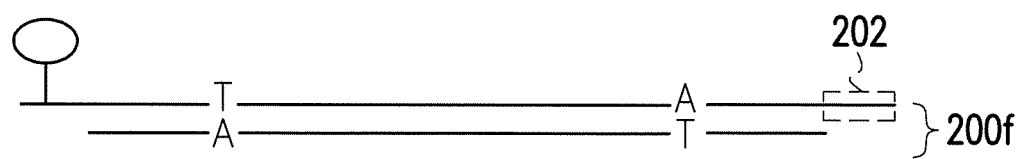

Referring to FIG. 4D, the partially double stranded linear DNA molecules 200f are dissociated from the streptavidin beads 130. In some embodiments, a method of dissociating the partially double stranded linear DNA molecules 200f from the streptavidin beads 130 includes a heating process. The partially double stranded linear DNA molecules 200f include single stranded protruding portions 202 at both ends.

Figure 4E:
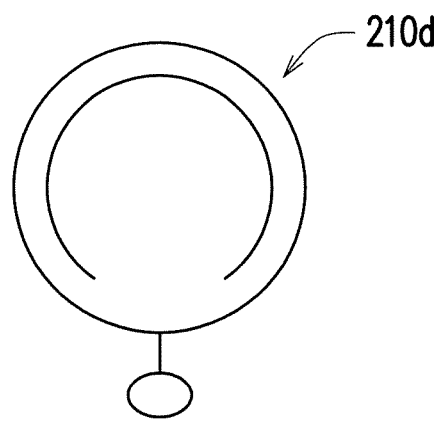

Referring to FIG. 4E, ligases are used to ligate the single stranded protruding portions 202 of the partially double stranded linear DNA molecules 200f, to generate partially double stranded circular DNA molecules 210d. In some embodiments, the partially double stranded circular DNA molecule 210d includes a single strand circular DNA molecule and a single strand linear DNA molecule which are formed from the double stranded linear DNA molecules 300 and adaptors (420, 440).

Then, the partially double stranded circular DNA molecules 210d are sequenced. In some embodiments, the linear strand of the partially double stranded circular DNA molecules 210d is directly used as a primer for sequencing, and thus additional priming step can be omitted.

FIGS. 5A-5E illustrate the method of detecting DNA molecules according to an embodiment of the invention.

Referring to FIG. 5A, DNA molecules, preferably fragmented DNA, such as cell free DNA molecules (140, 142) and oligonucleotides 150 are provided. In some embodiments, the cell free DNA molecules (140, 142) are single stranded linear DNA molecules derived from double stranded DNA molecules which are extracted from clinical specimens. The clinical specimens may be liquid biopsies or stool, and the liquid biopsies include plasma, saliva, or urine, for example.

In some embodiments, the cell free DNA molecules (140, 142) are nucleic acid samples extracted by column based or bead based nucleic acid extraction methods, such as QIAamp circulating NA, AccuBioMed, NextPrep-Mag cfDNA isolation kit (Bioo scientific), or Zinext. In some embodiments, the oligonucleotides 150 are adenylated.

Referring to FIG. 5B, the oligonucleotides 150 are ligated to the cell free DNA molecules (140, 142), and then ligated products are amplified to form amplicates (140', 142'). In some embodiments, the oligonucleotides 150 are ligated to 3' end of the cell free DNA molecules (140, 142). In some embodiments, the amplicates (140', 142') are formed by a uni-direction linear amplification method using primers paired with the oligonulceotides 150, for example. The amplicates (140', 142') include n copies of the cell free DNA molecules (140, 142), for example.

Figure 5C:
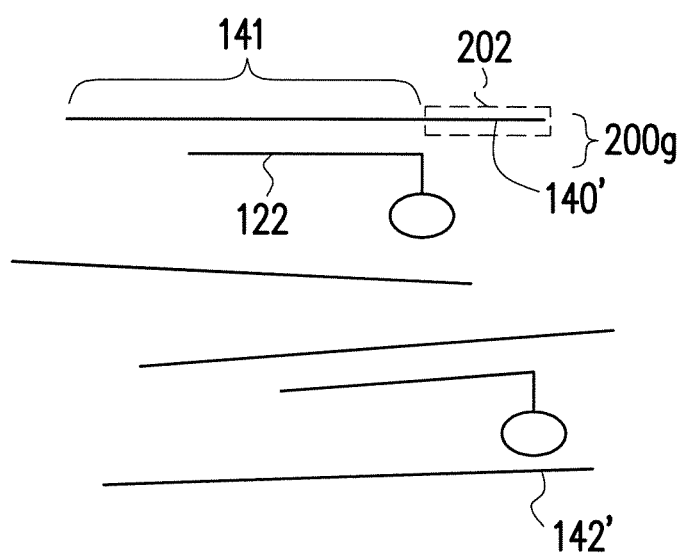

Referring to FIG. 5C, target DNA molecules 141 of the amplicates 140' are captured by sequence specific probes 122, so as to form the partially double stranded linear DNA molecules 200g. The partially double stranded linear DNA molecules 200g include single stranded protruding portions 202 at both ends. In some embodiments, the target DNA molecules 141 include a region of interest. In some embodiments, the sequence specific probes 122 are biotinylated probes, for example. In detail, the sequence specific probes 122 are hybridized to the target DNA molecules 141 of the amplicates 140', so as to form the partially double stranded linear DNA molecules 200g. Preferably, the amplicates 140' are single stranded DNA molecules with 40~500 nucleotides in length, and the sequence specific probes 122 are single stranded DNA molecules with 20~120 nucleotides in length. In some embodiments, the amplicates 140' are single stranded DNA of about 100 nucleotides in length, and the sequence specific probes 122 are single stranded DNA molecules with 20, 40, or 60 nucleotides in length.

Figure 5D:
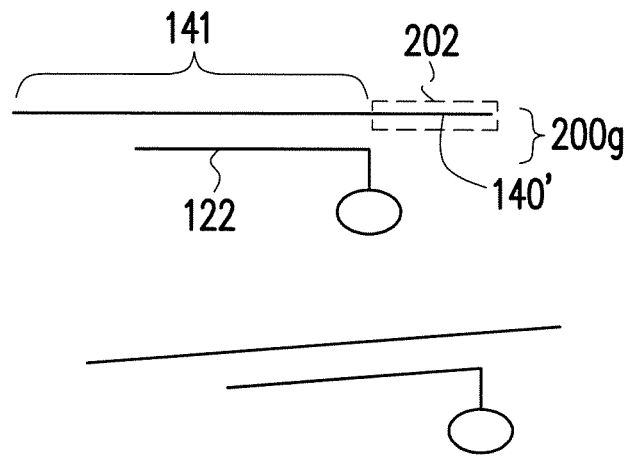

Referring to FIG. 5D, streptavidin beads (not shown) are used to extract the partially double stranded linear DNA molecules 200g which are hybridized with the biotinylated probes 122. The amplicates 142' which are not hybridized with the sequence specific probes 122 are removed by buffer washing. After extracting, the partially double stranded linear DNA molecules 200g are dissociated from the streptavidin beads 130 by a dissociating method such as a heating process.

Figure 5E:
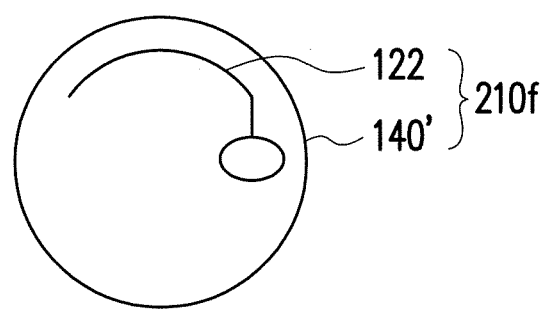

Referring to FIG. 5E, the ligases are used to ligate the single stranded protruding portions 202 of the partially double stranded linear DNA molecules 200g to generate partially double stranded circular DNA molecules 210f. In some embodiments, the partially double stranded circular DNA molecules 210f can be further amplified and/or analyzed. In some embodiments, the partially double stranded circular DNA molecules 210f is directed to circular sequencing analysis.

Then, the partially double stranded circular DNA molecules 210f are sequenced. In some embodiments, the sequence specific probes 122 can serve as primers for sequencing, and thus additional primers are not required.

To sum up, the invention provides a method of constructing a circular template for sequencing and a method of detecting DNA molecules by forming partially double stranded circular DNA molecules. The partially double stranded circular DNA molecules can be directed to circular amplification or circular sequencing. In some embodiments, the shorter strand DNA may act as a primer directly, and thus the methods have the advantage of high accuracy, rapid reaction, and low cost.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A method of constructing a circular template comprising:
   preparing a partially double stranded linear DNA molecule, wherein the partially double stranded linear DNA molecule comprises single stranded protruding portions at both ends on a same strand; and
   incubating the partially double stranded linear DNA molecule with a ligase capable of intra-molecular ligation of single stranded DNA molecules to generate a partially double stranded circular DNA molecule, wherein the ligase is single stranded DNA ligase, and the ligase is used to ligate the single stranded protruding portions of the partially double stranded linear DNA molecule so as to generate the partially double stranded circular DNA molecule.

2. The method as claimed in claim 1, wherein the step of preparing the partially double stranded linear DNA molecule comprises:
   providing a single stranded linear DNA molecule; and
   hybridizing a probe to the single stranded linear DNA molecule.

3. The method as claimed in claim 2, wherein the single stranded linear DNA molecule comprises 40 nucleotides to 500 nucleotides in length.

4. The method as claimed in claim 2, wherein the probe comprises 20 nucleotides to 120 nucleotides in length.

5. The method as claimed in claim 2, wherein the probe comprises a biotinylated probe.

6. The method as claimed in claim 5, after hybridizing the probe to the single stranded linear DNA molecule, further comprising extracting the partially double stranded linear DNA molecule by a streptavidin bead.

7. The method as claimed in claim 1, wherein the step of preparing the partially double stranded linear DNA molecule comprises:
   providing a double stranded linear DNA molecule;
   providing a first adaptor and a second adaptor, wherein the first adaptor and the second adaptor have a double stranded portion and a single stranded protruding portion at one end; and
   ligating the first adaptor to one end of the double stranded linear DNA molecule and the second adaptor to the other end to form the partially double stranded linear DNA molecule, wherein the single stranded protruding portion of the first adaptor and the single stranded protruding portion of the second adaptor are then on the same strand of the partially double stranded linear DNA molecule.

8. The method as claimed in claim 7, wherein the first and the second adaptors comprise at least 20 nucleotides of single stranded protruding portion at one end.

9. The method as claimed in claim 7, wherein the first adaptor or the second adaptor is conjugated with a biotinylated label, and the partially double stranded linear DNA molecule is then extracted by a streptavidin bead.

10. The method as claimed in claim 2, further comprising a step of removing the single stranded DNA molecules which are not hybridized with the probes.

11. The method as claimed in claim 1, wherein the partially double stranded linear DNA molecule comprises at least 10 nucleotides of single stranded protruding portions at the both ends.

\* \* \* \* \*